(12) United States Patent
Austin et al.

(10) Patent No.: US 7,961,328 B2
(45) Date of Patent: Jun. 14, 2011

(54) MULTIPLE-ANGLE RETROREFLECTOMETER

(75) Inventors: Richard L. Austin, Del Mar, CA (US); Charles L. Lustenberger, Oro Valley, AZ (US); Erik Stauber, San Diego, CA (US)

(73) Assignee: Belfort Instrument Company, San Diego, CA (US)

( * ) Notice: Subject to any disclaimer, the term of this patent is extended or adjusted under 35 U.S.C. 154(b) by 588 days.

(21) Appl. No.: 11/817,014

(22) PCT Filed: Feb. 27, 2006

(86) PCT No.: PCT/US2006/007034
§ 371 (c)(1),
(2), (4) Date: Sep. 3, 2008

(87) PCT Pub. No.: WO2006/091968
PCT Pub. Date: Aug. 31, 2006

(65) Prior Publication Data
US 2009/0116018 A1 May 7, 2009

Related U.S. Application Data

(60) Provisional application No. 60/656,210, filed on Feb. 25, 2005.

(51) Int. Cl.
*G01N 21/55* (2006.01)
(52) U.S. Cl. .................................................. 356/445
(58) Field of Classification Search .......... 356/445–448
See application file for complete search history.

(56) References Cited

U.S. PATENT DOCUMENTS

| | | |
|---|---|---|
| 4,368,982 A | 1/1983 | Van Arnam et al. |
| 4,373,819 A | 2/1983 | Pallotta |
| 4,721,389 A | 1/1988 | Dejaiffe |
| 5,410,407 A | 4/1995 | Zielinski et al. |
| 6,055,490 A | 4/2000 | Dunne |

(Continued)

OTHER PUBLICATIONS

International Search Report and Written Opinion dated Feb. 16, 2007, for International Application No. PCT/US06/07034, 5 sheets.

*Primary Examiner* — Michael P Stafira
(74) *Attorney, Agent, or Firm* — Christie, Parker & Hale, LLP (57) ABSTRACT

A system and method for measuring the photometric retroreflectivity of materials. The system comprises a light source and a first optical pathway along which an illumination light beam travels originating from the light source, and ending at a retroreflective surface to be measured. A second optical pathway is provided along which a retroreflected beam travels back from the retroreflective surface to an aperture array that selects multiple annular areas to be further directed to multiple detectors, one detector for each annular area selected by the aperture. Each detector has a filter for the determination of photometric retroreflectivity. The retroreflected light reaching the detectors produces currents proportion to the intensity of the light. A high-gain current-to-voltage amplifier is used to provide voltage signal to an analog-to-digital converter that converts a voltage to a digital number. A processor is electrically coupled to the analog-to-digital converter with an accompanying memory on which is stored operating logic adapted to determine the photometric intensity of a predetermined pattern of the retroreflected beam incident to the array of apertures and detectors which defines the retroreflected light which propagates from the retroreflective surface at a predetermined observation angle.

19 Claims, 6 Drawing Sheets

U.S. PATENT DOCUMENTS

| | | |
|---|---|---|
| 6,166,813 A | 12/2000 | Roberts |
| 6,212,480 B1 | 4/2001 | Dunne |
| 6,618,132 B1 | 9/2003 | Vann |
| 6,674,878 B2 * | 1/2004 | Retterath et al. ............ 382/104 |
| 6,891,960 B2 | 5/2005 | Retterath et al. |
| 6,946,643 B1 | 9/2005 | Fayfield |
| 7,030,365 B2 | 4/2006 | Langland |
| 2002/0186865 A1 | 12/2002 | Retterath et al. |
| 2004/0156531 A1 | 8/2004 | Retterath et al. |
| 2005/0088742 A1 | 4/2005 | Fujiwara et al. |
| 2005/0249378 A1 | 11/2005 | Retterath et al. |

* cited by examiner

MULTIPLE-ANGLE RETROREFLECTOMETER

CROSS-REFERENCE TO RELATED APPLICATIONS

This application is a National Phase Patent Application of International Application number PCT/US2006/07034, filed on Feb. 27, 2006, which claims priority of Provisional U.S. Patent Application No. 60/656,210, filed Feb. 25, 2005.

BACKGROUND OF THE INVENTION

This invention relates to a portable retroreflectometer for measuring the optical characteristics in multiple-angle point and annular geometry of retroreflective materials as typically used to male highway signs and safety markers. Unlike conventional reflection plane mirrors which reflect incident light back toward the source only if the incident light beam is perpendicular to the mirror surface, retroreflective materials reflect a non-perpendicular incident beam back toward the source. Elevated highway signs and markers illuminated by vehicle headlights can thus be seen and understood by a driver (whose eyes are positioned above the illuminating headlights) of the vehicle. The retroreflectometer enables verification of the optical characteristics of new signs and markers, and also the level of degradation of retroreflectivity of a worn, weathered, dirty, or otherwise partially obscured sign or marker.

SUMMARY OF THE INVENTION

A portable retroreflectometer instrument for measuring the characteristics of light reflected from a retroreflective surface of a road sign, marker, or similar surface to verify that incident light from vehicle headlights is visable to a driver positioned above the headlights. The instrument measures the intensity and characteristics of two or more annular bands of retroreflected light, and provides display and storage of the resulting data, and information on the condition of the retroreflective surface.

DETAILED DESCRIPTION OF THE PREFERRED EMBODIMENT

Figure 1:
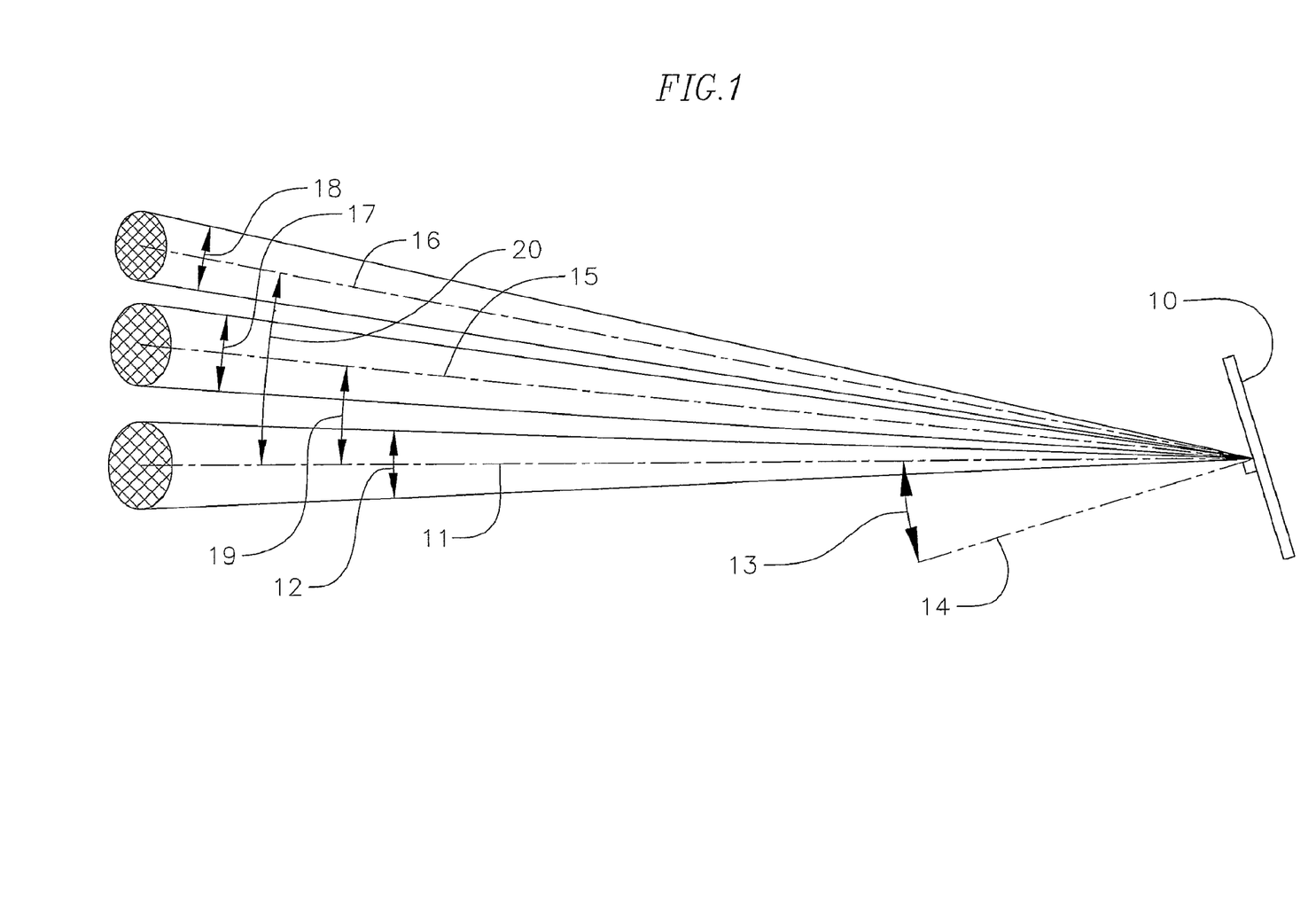
FIG. 1 shows the point-measurement relationship of incident and retroreflected light beams at two observation angles.

FIG. 1 shows a side view of a planar retroreflective surface 10 as used in highway signs and markers. An incoming illuminating light beam having a central axis 11 and a source aperture 12 strikes surface 10 at an entrance angle 13 which is the angle between axis 11 and a line 14 perpendicular to the planar surface. The drawing shows two retroreflected beams with central axes 15 and 16, and receiver aperture angles 17 and 18, the point-measurement beams being retroflected at observation angles 19 and 20 as subtended between central axis 11 and axes 15 and 16.

These geometric relations are well known (see, e.g., U.S. Pat. No. 6,166,813-Roberts, the disclosure of which, for brevity, is incorporated herein by reference) in the prior art. The need for measurements of multiple observation angles is dictated by the variable vertical spacing between the vehicle headlights, and the driver's eyes. This spacing is relatively small in a conventional passenger automobile, but larger in an SUV or truck where the driver is seated higher the road, resulting in a larger observation angle.

For example, certain U.S. measurement standards require measurements of retroreflective surfaces at observation angles of 0.2 and 0.5 degrees, with an entrance angle of 4 degrees. European standards vary somewhat, an entrance angle of 5 degrees, and an observation angle of 0.33 degrees being typical. The instrument of this invention can accommodate all of these requirements.

Figure 2:
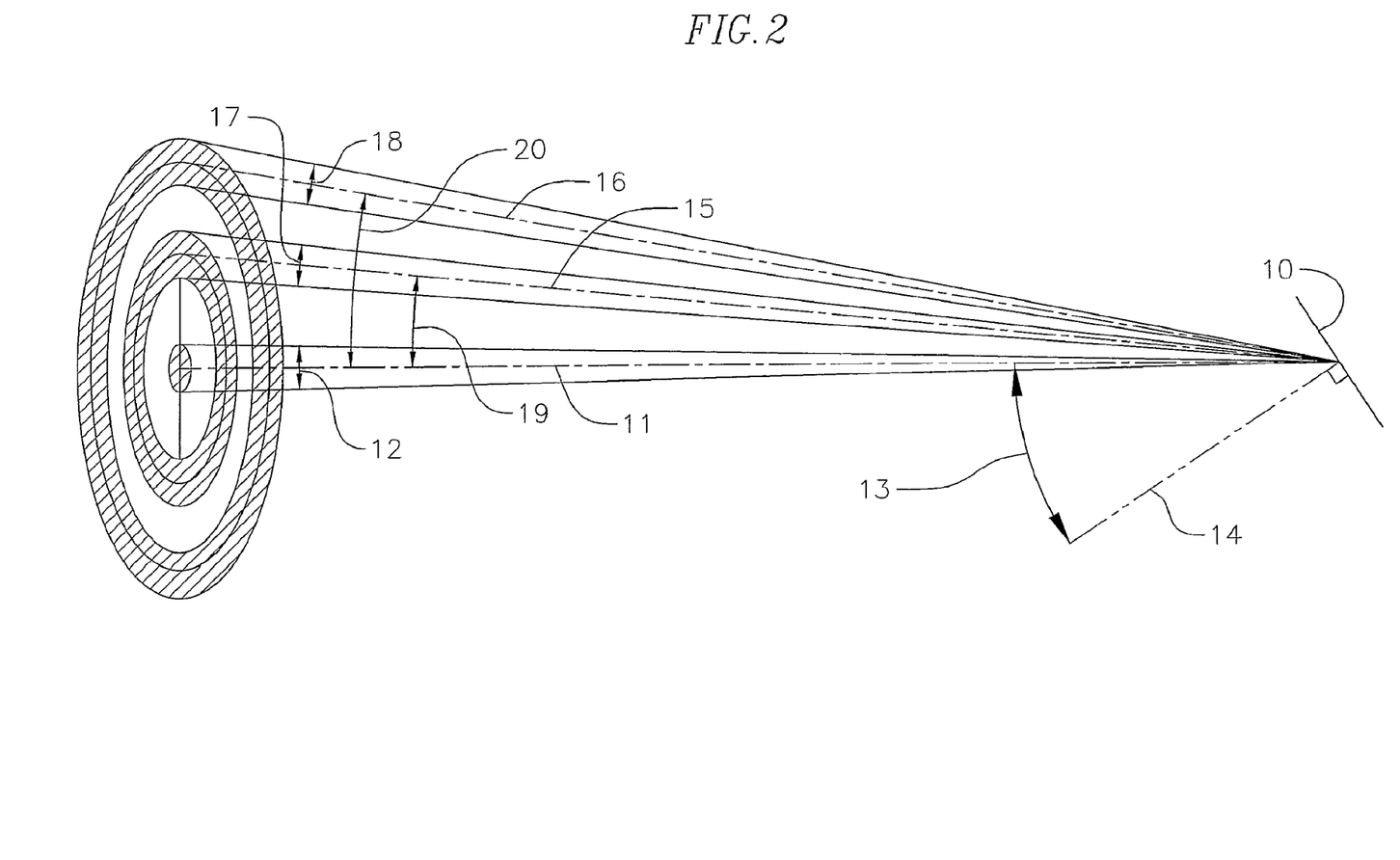
FIG. 2 shows the annular-measurement relationship of incident and retroreflected light beams at two observation angles.

FIG. 2 is similar to FIG. 1, and the several axes and angles are correspondingly designated, but the drawing illustrates annular measurements of annular reflected beams 21 and 22. The annular measurements enable a more comprehensive evaluation of the retroreflected light which reaches the variably positioned eyes of the driver.

Figure 3:
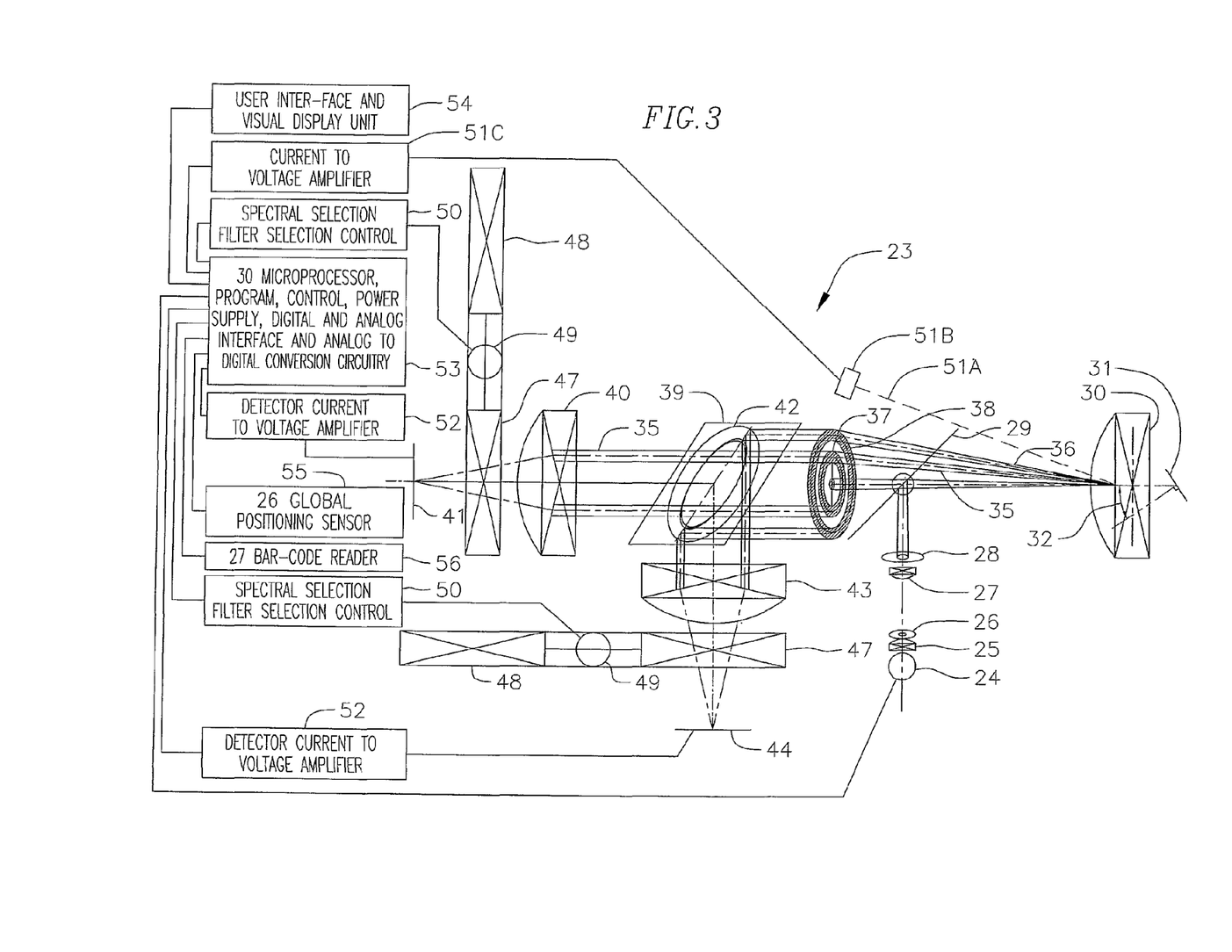
FIG. 3 is a schematic depiction of the components of a multiple-angle retroreflectometer.

FIG. 3 is a schematic illustration of one arrangement of the components of a multiple-angle retroreflectometer 23 according to the invention. A light source 24, typically a tungsten-filament lamp, emits light through a field lens 25 and a field aperture 26 which defines the size of the measurement area. The light beam continues through a light-projector objective lens 27 and source-angle definition aperture 28 to strike a beam splitter 29 (alternatively a small centrally positioned mirror) oriented at a 45-degree angle, which reflects the beam through an objective lens 30 to a retroreflective surface 31 at an observation angle 32.

Retroreflected inner-and-outer annular beams 35 and 36 pass through clear annular measurement areas 37 and 38 of a definition aperture. Inner annular beam 35 passes through a transparent plate 39 to a detector field lens 40 to be focused on a detector 41 which converts light intensity to an electrical current. Outer beam 36 is deflected 90 degrees by an annular mirrored surface 42 on plate 39 to a detector field lens 43 to be focused on a similar detector 44.

In an alternative embodiment, a spectral selection filter 47 can be interposed between either or both of the detector field lenses and the detectors to enable measurement of photometric or colorimetric values. Additional filters, typified by filter 48, can be selectively thus interposed by a filer selection mechanism 49 with an operator control 50. The light source and filter combinations preferably match CIE/ISO Illuminate A standard for spectral power distribution in the visible spectrum of 380-740 nanometers wavelength. The light source filter, and detector combination preferably meets this standard convolved with CIE 1931 Standard Photometric Observer function. The filters enable a detection response matching the spectral response of human eyes.

A peripheral portion of the retroreflected light with a centerline 51A illuminates a colorimetric detector 51B (an RGB Tri Color Sensor photodiode S8752 as marketed by Hamamatasu Photonics KK is suitable) which delivers to a current-to-voltage amplifier 51C three signals representing the intensities of red, blue, and green portions of the retroreflected spectral distribution. The output of amplifier 51C is delivered to microprocessor 50, enabling generation of a correction factor representing the color of the retroreflective sheet material.

Current outputs from detectors 41, 44 and the colorimetric detector are delivered to detector current-to-voltage amplifiers 52, the outputs of which are delivered to a microprocessor 53 with associated controls, memory, power supply and analog-to-digital converter. The microprocessor is coupled to user-interface and visual-display components 54. Preferably, the microprocessor is also coupled to a global position sensor 55, and a bar-code reader 56. Sensor 55 enables recordation of the location of the sign or marker being measured. Reader 56 detects and stores a bar code unique to each sign or marker as typically displayed on a back surface of the retroreflective material.

The system is not restricted to simultaneous measurement of two annular areas of illumination, and additional annular areas can be formed and measured by addition of the components described above.

Figure 4:
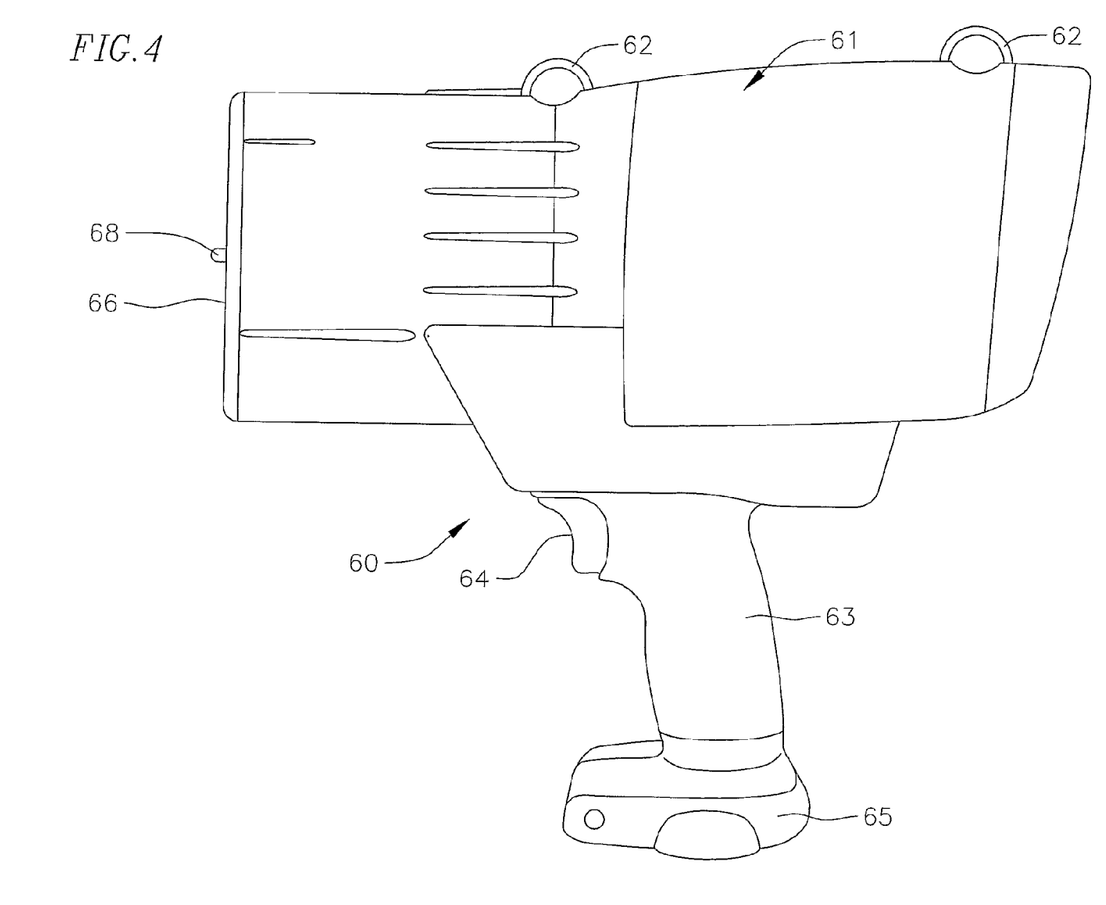
FIG. 4 is a side view of a retroreflectometer-instrument housing embodying the invention.
Figure 5:
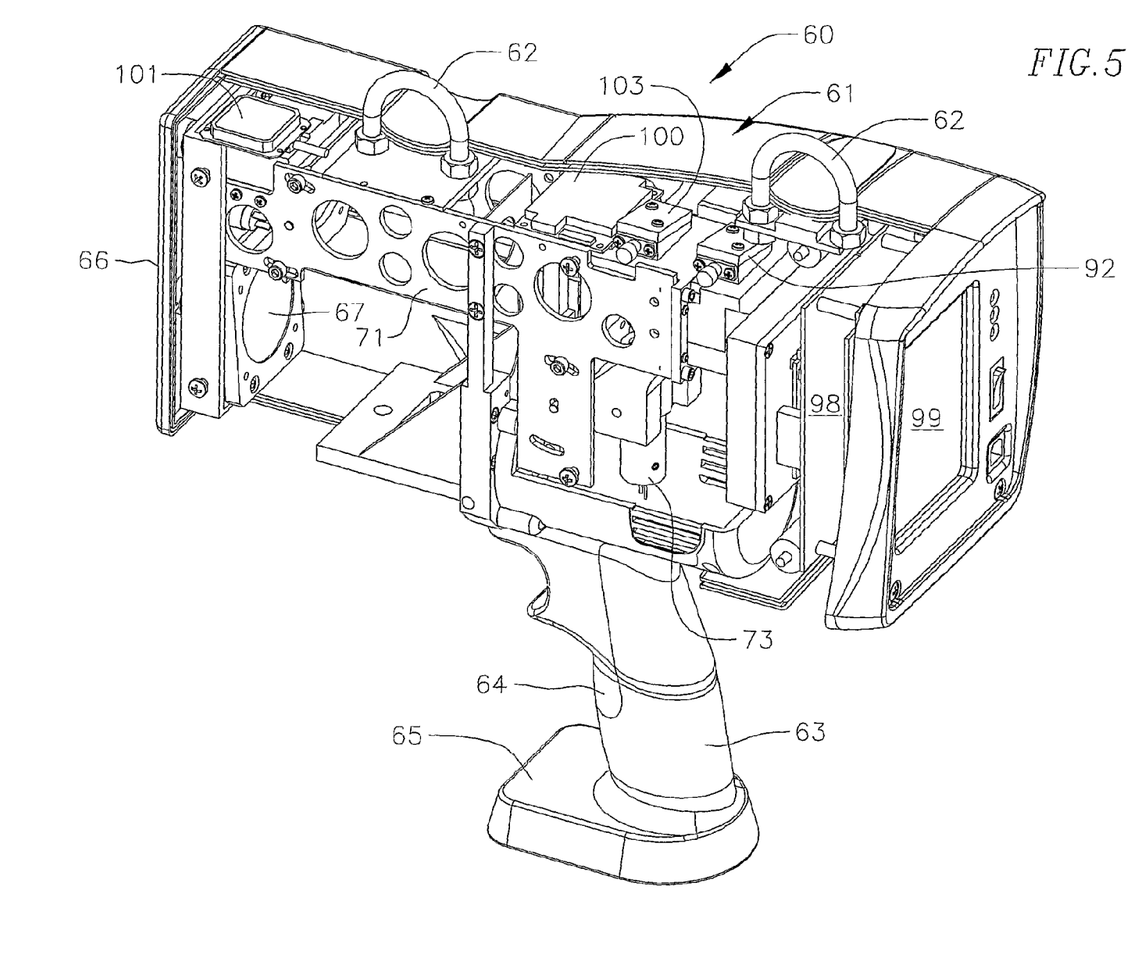
FIG. 5 is a perspective view of the instrument shown in FIG. 4, and with the housing partly broken away.
Figure 6:
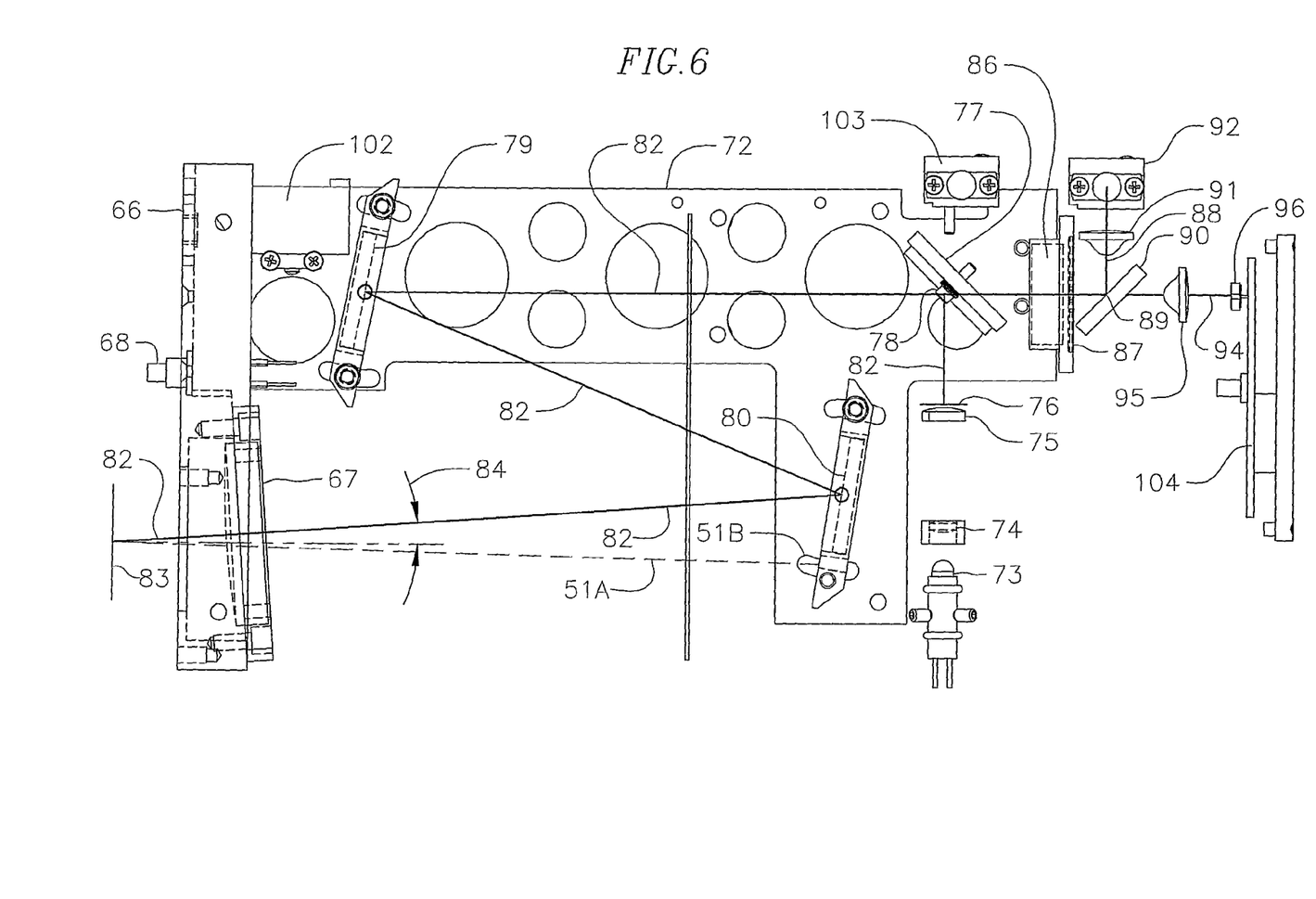
FIG. 6 is a side elevation of the optical components of the instrument.

FIGS. 4-6 illustrate a presently preferred embodiment of a retroreflectometer instrument 60 according to the invention. As shown in FIG. 4, the instrument has an outer housing 61 having an upper surface with a pair of hooks 62 for a shoulder strap. A pistol-grip handle 63 extending beneath the housing has an actuating trigger 64, a base 65, and a removable and interchangeable battery (not shown). A housing front panel 66 carries an objective lens 67 (FIGS. 5 and 6) and a push-button switch 68 which signals when the front panel is positioned against the retroreflective material being measured.

Internal components of instrument 60 are shown in FIGS. 5 and 6. FIG. 5 shows the instrument with the left side of housing 61 broken away. A pair of laterally spaced-apart left and right frames 71 and 72 mount instrument components therebetween, and only left frame 71 is shown in FIG. 5, right frame 72 being shown in FIG. 6.

The instrument internal components are best seen in FIG. 6. A tungsten-filament illumination lamp 73 or similar light source projects a light beam through a field aperture (defining the measurement size) and lens 74 to a light-projector objective lens 75 and an angular-definition aperture 76 to a non-polarizing beam-splitter panel 77 with a central reflecting mirror 78. The outgoing light beam is deflected 90 degrees (to the left in FIG. 6) to a first front-surface plane mirror 79 which is angled to deflect the reflected beam downwardly and to the right to a second front-surface mirror 80 which is angled to deflect the beam downwardly and to the left to objective lens 67. Mirrors 79 and 80, and objective lens 67 are adjustably mounted between frames 71 and 72.

The focused light beam with a centerline 82 impinges on a retroreflective surface 83 being measured, and at an entrance angle 84. The retroreflected collimated beam of about one-inch diameter returns via first and second mirrors 79 and 80 to pass straight through beam-splitter 77 and an optional photometric filter assembly 86, and then through an annular definition aperture 87. This aperture defines at least two annular areas of retroreflected illumination, typically at observation angles of 0.2 and 0.5 degrees.

The smaller illuminated annular beam is deflected 90-degrees upwardly along a centerline 88 by a small central mirror 89 on an otherwise transparent panel 90 to a first detector field lens 91 which focuses the beam on a first detector 92 which converts light intensity to an electrical current as described above. The larger illuminated annular beam with a centerline 94 passes straight through transparent panel 90 and a second detector field lens 95 to a second detector 96. As already described, the detector current signals are converted to voltages, digitized, and delivered to a microprocessor for display, storage, averaging, and the like. The instrument is not limited to measurement of two annular areas of retroreflected light, and additional areas can be measured by modifying annular definition aperture 87, and adding additional field lenses and detectors.

Further instrument components depicted in FIG. 5 and/or FIG. 6 include a microprocessor 98, a graphical user-interface touchscreen 99, a global-position sensor 100 and associated GPS antenna 101, a bar-code scanner 102, an illuminating-lamp reference diode 103, and a detector current-to-voltage converter and associated digitizer 104.

There has been described a versatile instrument for measuring intensity of retroreflected light in multiple annular areas of illumination. The instrument broadly comprises an optical system for illuminating a retroreflective surface and focusing the retroreflected light into annular zones for measurement, and an electronics system (microprocessor with storage detectors and digitizers, GPS and bar-code components, touchscreen and controls, etc.) enabling display, averaging, and storage of intensity levels, sign position and identification, and the like. Spot measurements can of course be made if desired by modifying the aperture which defines the retroreflected light reaching the detectors.

What is claimed is:

1. A portable handheld instrument for measuring the retroreflectivity of a surface such as a highway sign or marker configured to be illuminated by vehicle headlights, comprising:
 a housing;
 an optical system supported by the housing, the optical system configured to illuminate the retroreflective surface and to focus a retroreflected light, comprising light reflected from the retroreflected surface, into at least two annular zones; and
 an electronic system supported by the housing for measuring and processing signals representing an intensity of the retroreflected light in the several annular zones.

2. The instrument of claim 1, and further comprising a global-positioning sensor for determining a location of the retroreflective surface being measured, and a bar-code sensor for detecting and storing a bar code unique to the surface being measured.

3. The instrument of claim 1, wherein the electronic system includes a touch-screen display and touch-screen controls, and a microprocessor for digitizing and processing of the several signals representing the intensity of the retroreflected light.

4. The instrument of claim 1, further comprising a colorimetric light-sensor means for detecting color distribution in the retroreflected light to enable determination of a color of the retroreflective surface.

5. The instrument of claim 4, wherein the colorimetric light-sensor means comprises a color sensitive photodiode.

6. The instrument of claim 5, wherein the color sensitive photodiode is configured to measure the spectral distribution of the retroreflected light in the red, blue, and green portions of the visible spectrum.

7. The instrument of claim 5, wherein the color sensitive photodiode is configured to generate information indicative of the color of the retroreflective surface.

8. The instrument of claim 7, wherein the generated information comprises a color value defined by the CIE 1931 colorimetric coordinate system.

9. The instrument of claim 1, wherein the optical system comprises a means for directing a retroreflected light beam to pass through the at least two annular zones.

10. The instrument of claim 9, wherein the means for directing the retroreflected light beam comprises an annular definition aperture defining the at least two annular zones.

11. The instrument of claim 9, wherein the means for directing the retroreflected light beam comprises a photometric filter for measurement of photometric or colorimetric values.

12. The instrument of claim 11, wherein the photometric filter is configured to filter light in accordance with the CIE 1931 Standard Observer function.

13. The instrument of claim 11, wherein the photometric filter is configured to enable a detection response matching a spectral response of a human eye.

14. The instrument of claim 9, wherein the means for directing the retroreflected light beam comprises a plate having a surface comprising an annular transparent portion and an annular mirrored portion.

15. The instrument of claim 14, wherein the plate is configured to enable the retroreflected light focused in one of the two annular zones to pass through the annular transparent portion.

16. The instrument of claim 15, wherein the plate is configured to reflect the retroreflected light focused in one of the two annular zones from the annular mirrored portion.

17. The instrument of claim 14, wherein the annular mirrored portion comprises an annular ring that encircles the annular transparent portion.

18. The instrument of claim 9, wherein the means for directing the retroreflected light beam comprises:
   an annular definition aperture defining the at least two annular zones;
   a photometric filter for measurement of photometric or colorimetric values,
   wherein the photometric filter is attached to the annular definition aperture.

19. The instrument of claim 1, wherein the electronic system comprises:
   photosensitive detectors for generating signals representing the intensity of the retroreflected light in the several annular zones;
   means for digitalizing the generated signals; and
   a microprocessor for comparing, displaying, and storing the digitized signals.

* * * * *

UNITED STATES PATENT AND TRADEMARK OFFICE
CERTIFICATE OF CORRECTION

PATENT NO.        : 7,961,328 B2                                            Page 1 of 1
APPLICATION NO.   : 11/817014
DATED             : June 14, 2011
INVENTOR(S)       : Richard L. Austin et al.

It is certified that error appears in the above-identified patent and that said Letters Patent is hereby corrected as shown below:

On the Title Page:

Item (73) Assignee:         Delete "Belfort Instrument Company"
                            Insert -- Gamma Scientific Inc. --

Signed and Sealed this
Tenth Day of April, 2012

David J. Kappos
*Director of the United States Patent and Trademark Office*